United States Patent [19]

Zardi

[11] Patent Number: 4,670,588

[45] Date of Patent: Jun. 2, 1987

[54] PROCESS FOR THE PRODUCTION OF UREA

[75] Inventor: Umberto Zardi, Lugano, Switzerland

[73] Assignee: Ammonia Casle S.A., Lugano, Switzerland

[21] Appl. No.: 640,243

[22] Filed: Aug. 13, 1984

Related U.S. Application Data

[63] Continuation of Ser. No. 402,292, Jul. 27, 1982, abandoned.

[30] Foreign Application Priority Data

Oct. 16, 1981 [IT] Italy .............................. 24526 A/81

[51] Int. Cl.$^4$ .......................................... C07C 126/02
[52] U.S. Cl. ....................................... 564/72; 564/70; 564/71
[58] Field of Search ........................ 564/67, 71, 72, 70

[56] References Cited

U.S. PATENT DOCUMENTS

| | | | |
|---|---|---|---|
| 3,607,938 | 9/1971 | Braun ..................................... | 564/70 |
| 3,984,469 | 10/1976 | Guadalupi et al. ................... | 564/72 |
| 4,066,693 | 1/1978 | Venderbos ........................ | 564/70 X |
| 4,137,262 | 1/1979 | Gaudalupi et al. .................. | 564/72 |
| 4,208,347 | 1/1980 | Pagani .................................. | 564/70 |
| 4,314,077 | 2/1952 | Zardi et al. ........................... | 564/70 |

Primary Examiner—Robert V. Hines
Attorney, Agent, or Firm—Holman & Stern

[57] ABSTRACT

A process for the synthesis of urea from ammonia and carbon dioxide in which high yield reaction and optimal reactor heat balance control are achieved at the same time by using two reaction zones, where two different $NH_3/CO_2$ molar ratios are maintained, and by treating the effluent from the second reaction zone in a separation treatment in two steps in series; the reactant gas stream discharged from the second treatment step is recycled, after partial condensation, to the first reaction zone, while at least part of the gas stream discharged from the first treatment step is recycled directly to the second reaction zone, the gas stream from both the first and second treatment step being so controlled as to obtain optimal $NH_3/CO_2$ ratios and optimal reaction temperatures in the two reaction zones.

2 Claims, 4 Drawing Figures

PROCESS FOR THE PRODUCTION OF UREA

This is a continuation of application Ser. No. 06/402,292, filed Jul. 27, 1982 and now abandoned.

BACKGROUND OF THE INVENTION

1. Field of the Invention

This invention relates to a urea production process by synthesis where ammonia ($NH_3$) and carbon dioxide ($CO_2$) are reacted under high pressure and at a high temperature to form urea, ammonium carbamate, water and unreacted compounds, and in which reacted effluents discharged from the said synthesis reactor are treated to decompose the carbamate and recover the unreacted compounds in order to recycle them to the reactor; more specifically, the invention relates to a urea production process with low energy consumption, high reaction yields and low residual content of unreacted material in the urea produced.

2. Description of the Prior Art

It is known that high reaction yeilds are favoured by a high ammonia excess (compared with the stoichiometric ratio), which require, however, a high reactor operating pressure. A high synthesis pressure is unfavourable to the efficient separation of unreacted compounds from the urea solution obtained. In consequence before the so-called "stripping" technology, in which the bulk of unreacted components are separated in steps operating at reactor pressure by using a stripping agent ($NH_3$ and/or $CO_2$), became known pressure was drastically reduced downstream the reactor to achieve the efficient separation of the unreacted material.

In stripping processes the reactor operating pressure has been drastically reduced, to the detriment of yields, to a compromise pressure in order to achieve the isobaric separation of the unreacted material by using a stripping agent.

Several processes have been recently described, aiming to combine the advantages of high reaction yields typical of conventional processes with the advantages of stripping processes.

Among the most recent processes of this kind, the following might be mentioned:

(A) U.S. Pat. No. 4,208,347 (Montedison); (B) Japanese Patent Application PCT/JP 70/00192 (Mitsui T. and Toyo E.); (C) British Patent Application No. 2028311 (Ammonia Casale SA); (D) Italian Patent Application No. 24357A/80 (Snamprogetti).

It should be stated in advance that the forerunner of the above patent documents should be considered to be British Patent No. 1.1185.944 (Chemico) in which treatment of the bulk of the solution discharged from a high yield reactor is in two steps in series (only the first or both isobaric with the reactor); the bulk of the carbamate is separated in the first step also with the help of fresh stripping $NH_3$ and the residual $NH_3$ is separated in the second step with the introduction of fresh stripping $CO_2$.

The above processes according to (A), (B) and (C) have, downstream a urea reactor, two separation steps in series in which the unreacted compounds are separated "selectively": more specifically in (A) and (D) the bulk of the carbmate is separated in the first step and residual ammonia is separated in the second step using $CO_2$ as stripping agent; in (C) the bulk of the ammonia is separated in the first step and the carbamate is decomposed in the second step possibly with the help of $CO_2$ as stripping agent either in the second or in both steps.

This is achieved by operating under critical conditions in both separation steps. In the process according to (B) there are two separation steps downstream a high-yield reactor, in which the unreacted compounds are separated. As in processes (A) and (D), a falling film exchanger is used in the first step, using $NH_3$ as stripping agent. Similarly to (A) and (D), therefore, the bulk of the carbamate is selectively separated in the first step, while in the second step the residual reactants are separated, using $CO_2$ as stripping agent: a falling-film exchanger is used in both steps. In process (D), as a variation from process (A), the second treatment step is not isobaric with the rest of the loop (reactor in a single step isobaric with the first treatment step).

In process (A) all the vapours ($NH_3+CO_2$) obtained by decomposing carbamate (prevalently in the first step) are separated and recycled directly to the reactor (and, where the latter is in two sections, to the upper section), while the vapours obtained in the second step (residual free ammonia and stripping $CO_2$ fed to the falling film exchanger) are fully condensed and recycled to the reactor (upper section in the case of a two-section reactor).

In process (B) the vapours separated in the two steps downstream a conventional high-yield reactor are mixed and condensed before being recycled in solution form to the reactor by means of an ejector. In patent (A), although a reactor in two superimposed sections is described in one of the alternatives, the two streams of material separated in the two steps in series downstream the reactor are both recycled to the main reactor (upper section in the case of a two-section reactor) or simply to the single piece reactor. Even if, as is known, the two-step reactor is adopted to exploit the concept (known per se) of using several reaction zones with different $NH_3/CO_2$ molar ratios in order to optimize transformation yields, it does not solve satisfactorily from an economic point of view the important problem of heat balance control (operating temperature) in the two reaction zones; this problem, up to the present, has been the main obstacle preventing the effective application of these systems.

The heat balance problem becomes even more critical in high-yield reactors where it is necessary to operate with high $NH_3$ excesses, involving a greater lack of heat.

According to processes (A) and (D), moreover, since all gaseous compounds from the second treatment step are condensed before being recycled to the reactor, it is absolutely imperative, by reason of the reactor's heat balance, that practically all the carbamate should be separated in the first step, thus obtaining a sufficient amount of $CO_2$ in the gas stream recycled directly as such to the reactor, which ensures that sufficient heat is produced as reaction heat from forming carbamate. To achieve such selective separation of the bulk of the carbamate in the first step it is nevertheless necessary to use complex and expensive falling film exchangers and large quantities of stripping agent ($NH_3$) which, as described above, must be expensively evaporated.

In effect in process (A) there is also compensation for the insufficient heat balance in the two reaction steps by introduction in both steps of fresh feed ammonia, preheated and/or evaporated, thus using up energy and involving complex controls. It should also be pointed out that part of the fresh feed ammonia must also be sent to the first reactor effluent treatment stage as stripping agent to decompose the bulk of the carbamate. Both reaction zones therefore have insufficient heat, so that all the fresh feed ammonia must be uneconomically preheated and/or evaporated.

In process (B) the problem of the reactor's heat balance is ignored since all the carbamate (exothermic reaction, hence main source of heat) forms outside the reactor.

In process (C) this critical aspect, which nevertheless conditions and defines the recycling system for the unreacted compounds from the two treatment steps, is not described (because outside or not homogeneous with the essential aspect of the specific treatment according to the invention).

Both in process (A) and process (B) the high synthesis pressure required to produce high yields heavily conditions the separation efficiency of the unreacted compounds in the two treatment steps operating isobarically with the reactor.

SUMMARY OF THE INVENTION

The main object of this invention is to provide a process which does not suffer from the above-mentioned drawbacks and successfully combines a high-yield synthesis reaction with subsequent efficient separation of the compounds not transformed into urea in such reaction. Another object of the invention is to provide a process which, while providing a high-yield synthesis reaction, can at the same time carry out the efficient separation of the unreacted compounds and control the heat balance without the additional consumption of energy. A further object of the invention is to provide a process in which optimal reaction conditions ($NH_3/CO_2$ ratio, reaction temperature etc.) upstream the reactor are controlled by controlling treatment conditions downstream the reactor.

Finally, yet another object of the invention is to provide a process in which the pressure is so distributed in the various steps as to result in a high degree of operating flexibility and economy. These and other objects are achieved with the process according to the invention, characterized by the fact that since the synthesis reaction is carried out in two zones in series each with a different $NH_3/CO_2$ ratio, the whole of the reactant ($NH_3+CO_2$) stream leaving the second treatment step is recycled to the first of such zones after partial condensation, while at least part of the gas ($NH_3+CO_2$) stream leaving the first treatment step is recycled directly to the second reaction zone, the amount of gas leaving the first and second treatment step being controlled in such a way as to ensure optimal $NH_3/CO_2$ ratios and reaction temperatures in the two reaction zones.

A further feature of the invention is that the gas stream recovered in the second treatment step is partially or totally condensed and a portion of vapours from the first and/or second treatment step is sent directly to the first reaction zone so that the residual vapours provide by reaction, in both cases (total or partial condensation) the heat necessary to maintain at optimal value the temperature in the first reaction zone; in the same way, the first treatment step is controlled so as to produce the right gas to maintain at optimal value the $NH_3/CO_2$ ratio and temperature in the second reaction zone. Fresh $NH_3$ or $CO_2$ may possibly be introduced in the first treatment step. A particularly advantageous embodiment of the invention is that the operating pressure in the second reaction zone is equal to the pressure in the first treatment step while the pressure in the first reaction zone is equal to the pressure in the second treatment step and in the condenser, and preferably lower than the pressure in the second reaction zone and in the first treatment step. A high degree of operating flexibility and considerable energy saving are thus achieved.

BRIEF DESCRIPTION OF THE DRAWINGS

The various aspects and advantages of the invention will become more apparent from the description of the embodiments shown in the attached drawings and from the following examples, the embodiments and examples being an illustration and not a limitation of the invention. In said drawings

DETAILED DESCRIPTION OF THE PREFERRED EMBODIMENTS

Figure 1:
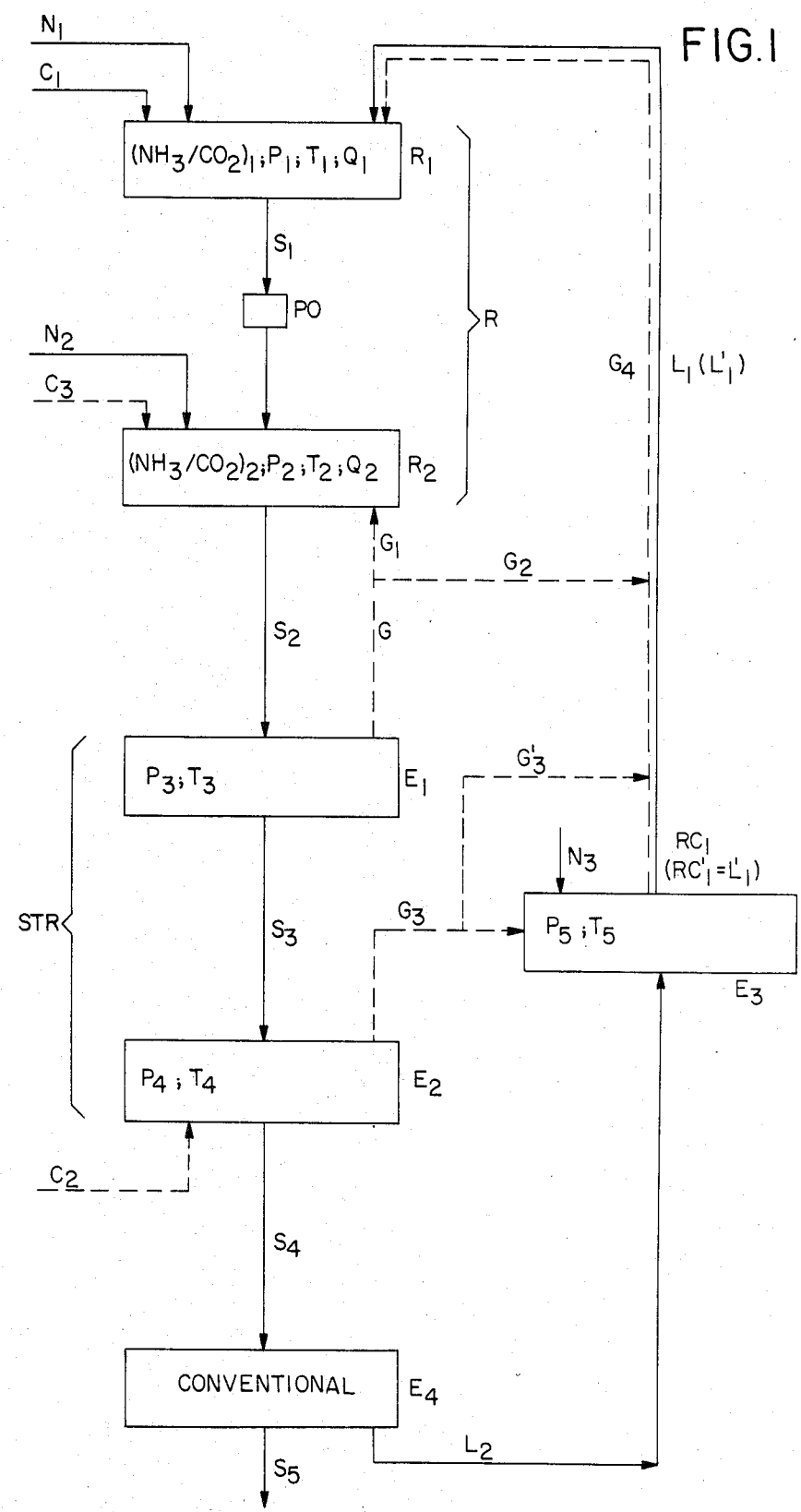
FIGS. 1 to 4 are block diagrams or schemes of the preferred process embodiments.

In the drawing in FIG. 1 the letter R indicate the whole synthesis reaction zone and the letters STR indicate the whole separation treatment zone for the stream from R.

This whole reaction zone R is now divided into at least two reaction zones: $R_1$ where reaction betwen fresh reactants $N_1$ (indicating the $NH_3$ feed stream) and $C_1$ (indicating the $CO_2$ feed stream) and the recycle stream (gas+liquid) $G_4+L_1$ (or $L'_1$ with $G_4=O$) takes place with molar ratio $(NH_3/CO_2)_1$, pressure $P_1$, temperature $T_1$ and therefore urea transformation yield $Q_1$; $R_2$ in which the synthesis reaction of stream $S_1$ from $R_1$, with the possible addition of fresh ammonia feed $N_2$ and/or carbon dioxide $C_3$ is completed at molar ratio $(NH_3/CO_2)$ 2, pressure $P_2$, temperature $T_2$ and yield $Q_2$. The effluent $S_2$ from the second reaction zone $R_2$ now undergoes a quantitative STR treatment, also in two steps, to decompose the carbamate and separate the unreacted compounds, consisting of: step $E_1$ where at selected operating pressure $P_3$ and temperature $T_3$ (besides residence time) an amount of gas G is separated, the bulk of which is recycled as stream $G_1$ directly to the second reaction step $R_2$ (the residual part $G_2$, if any, being sent through circuit $RC_1$ and/or directly to the first zone $R_1$; step $E_2$ in which effluent $S_3$ from the first treatment step $E_1$ is treated at pressure $P_4$, temperature $T_4$, preferably countercurrently with fresh carbon dioxide $C_2$ to to recover all the residual unreacted materials $G_3$ which after partial condensation in $E_3$ (operating at pressure $P_5$ and temperature $T_5$ with the possible addition of fresh ammonia $N_3$) are recycled as vapour-liquid mixture $G_4+L_1$ to the first reaction zone $R_1$. Alternatively condensation in $E_3$ may be total ($G_4=O$, recycle $RC'_1=L'_1$) and a portion of vapours $G_3 (=G'_3)$ is sent directly to the first reaction zone $R_1$. Effluent $S_4$ from $E_2$ is then conventionally treated in $E_4$ where the required final product $S_5$ is separated and solution $L_2$ is recycled to condenser $E_3$. With the process according to the invention an entirely isobaric scheme where $P_1=P_2=P_3=P_4=P_5$, or preferably a non-isobaric scheme can be achieved. With a non-isobaric scheme, to the advantage of maximum efficiency and flexibility $R_2$ and $E_1$ may be kept at the same pressure $P=P_2=P_3$, and $R_1$, $E_2$ and $E_3$ at the same pressure $P'=P_1=P_4=P_5$, P being higher than P'. The high pressure "P" is therefore maintained only in a small portion of the plant, with considerable savings in energy consumption and plant investment costs. At the same time as high pressure $P_2$, a high $(NH_3/CO_2)_2$ ratio will also be selected so as to achieve the highest yields.

According to the main feature of the invention, since the decomposition and separation treatment of the compounds unreacted in $E_1$ and $E_2$ is quantitative, such treatment is controlled so that both in the first ($E_1$) and in the second ($E_2$) step can be obtained directly those gas streams (G) and ($G_3$) which sent separately to the first and second reaction zone ensure optimal $(NH_3/CO_2)_1$ and $(NH_3/CO_2)_2$ ratios and optimal heat balances to achieve maximum yields and correct reaction temperature.

These high yields are advantageously achieved by minimizing the pressure in reactor R and, consequently, the pressure of the two steps in the isobaric scheme with maximum separation efficiency of the unreacted materials and minimum energy consuption and investment costs in the non-isobaric scheme where only the second reaction zone and the first treatment step operate at higher pressure.

Another advantage of the invention lies in the fact that, since the separation treatment is quantitative, the first step may be carried out inexpensively, i.e. without having to use a falling film separator.

EXAMPLES

Figure 2:
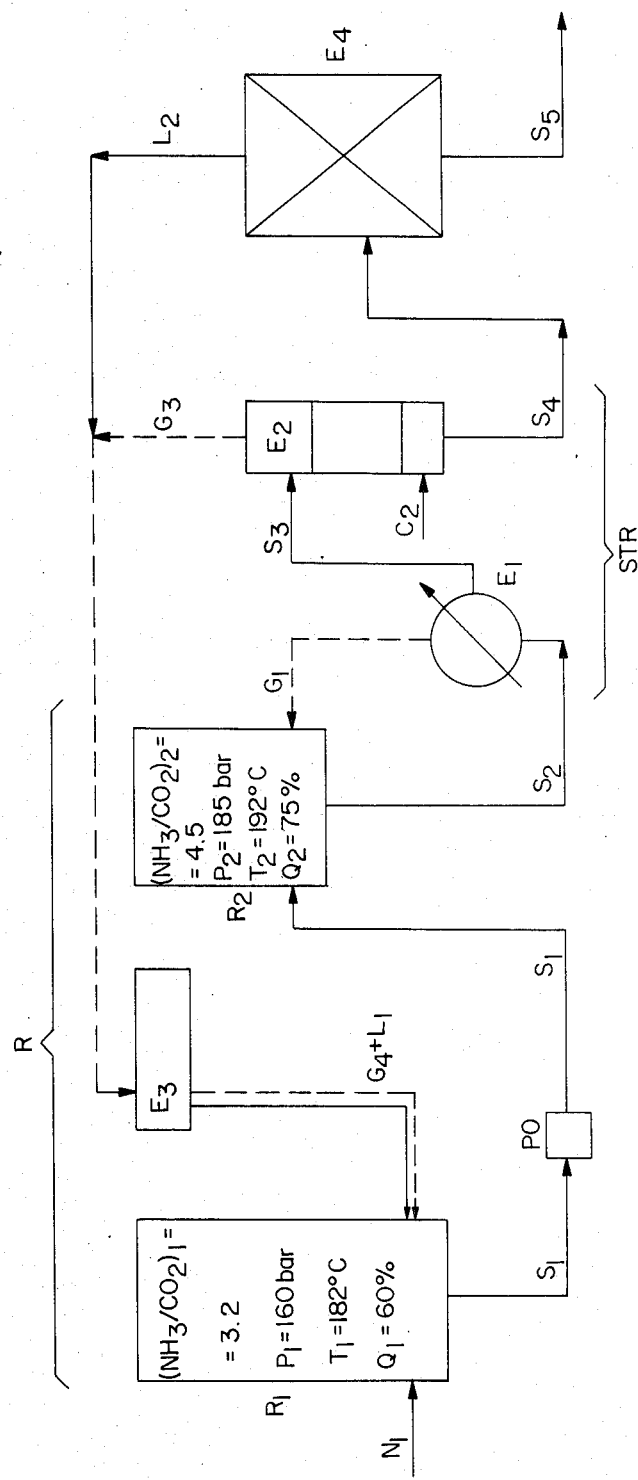

1. Non-isobaric operation (FIG. 2 and Table 1)

To the first reaction zone $R_1$ operating at $P_1=160$ bar and $T_1=182°$ C. are fed a 32.32 mole $NH_3$ stream $N_1$ at 40° C., and the liquid-vapour mixture $G_4=L_1$ containing 20 moles of $CO_2$, 30.68 moles of $NH_3$, 6 moles of $H_2O$ at 174° C.; the molar ratio $(NH_3/CO_2)_1$ is equal to 3.2 and the conversion yield $Q_1$ of $CO_2$ into urea is 60%. The urea solution $S_1$ feeding the second reaction zone $R_2$ consists therefore of 12 moles of urea, 8 moles of $CO_2$, 40 moles of $NH_3$ and 18 moles of $H_2O$.

To the second reaction zone $R_2$, operating at $P_2=185$ bar and $T_2=192°$ C., in addition to solution $S_1$ from the first zone $R_1$ fed for example through pump Po to overcome the pressure differential (from $P_1=160$ bar to $P_2=135$ bar) are fed vapours $G_1$ at 196° C. containing 2.2 moles of $CO_2$ and 36 moles of $NH_3$ and 1 mole of $H_2O$ coming from the first treatment step $E_1$ also operating at $P_3=185$ bar and at $T_3=196°$ C. In the second reaction zone $R_2$ the molar ratio $(NH_3/CO_2)_2$ is 4.5 and the $CO_2$ reaction yield $Q_2$ is 75%. The urea solution $S_2$ containing 16.66 moles of urea, 5.54 moles of $CO_2$, 66.68 moles of $NH_3$ and 23.66 moles of $H_2O$ feeds the first treatment step $E_1$ where at $P_3=P_2=185$ bar and at $T_3=196°$ C. are separated 2.2 moles of $CO_2$, 36 moles of $NH_3$ and 1 mole of $H_2O$, which are fed directly to the second reaction zpme $R_2$. Solution $S_3$, containing 16.66 moles of urea, 3.34 moles of $CO_2$, 30.68 moles of $NH_3$ and 22.66 moles of $H_2O$ feeds the second treatment step $E_2$ operating at $P_4=P_1=160$ bar and $T_4=185°$ C., where by using 16.66 moles of $CO_2$ countercurrently (indicated by $C_2$ in the drawing) are separated from the urea solution 1.84 moles of $CO_2$, 17.48 moles of $NH_3$ and 2 moles of $H_2O$.

The gas from $E_2$ consisting of 18.5 moles of $CO_2$, 47.48 moles of $NH_3$ and 2 moles of $H_2O$ feeds condenser $E_3$ (carbamate condenser), also fed from solution $L_2$, 1.5 moles of $CO_2$, 3.2 moles of $NH_3$ and 4 moles of $H_2O$, discharged from final treatment system $E_3$ where the last traces of $CO_2$ and $H_2O$ still contained in solution $S_4$ discharged from $E_2$ are finally separated. The mixed phase (vapours+carbamate solution)$G_4+L_1$ at 160 bar and 175° C. formed in condenser $E_3$ is recycled by gravity to the first reaction zone $R_1$. It contains 20 moles of $CO_2$, 30.68 moles of $NH_3$ and 6 moles of $H_2O$.

Figure 3:
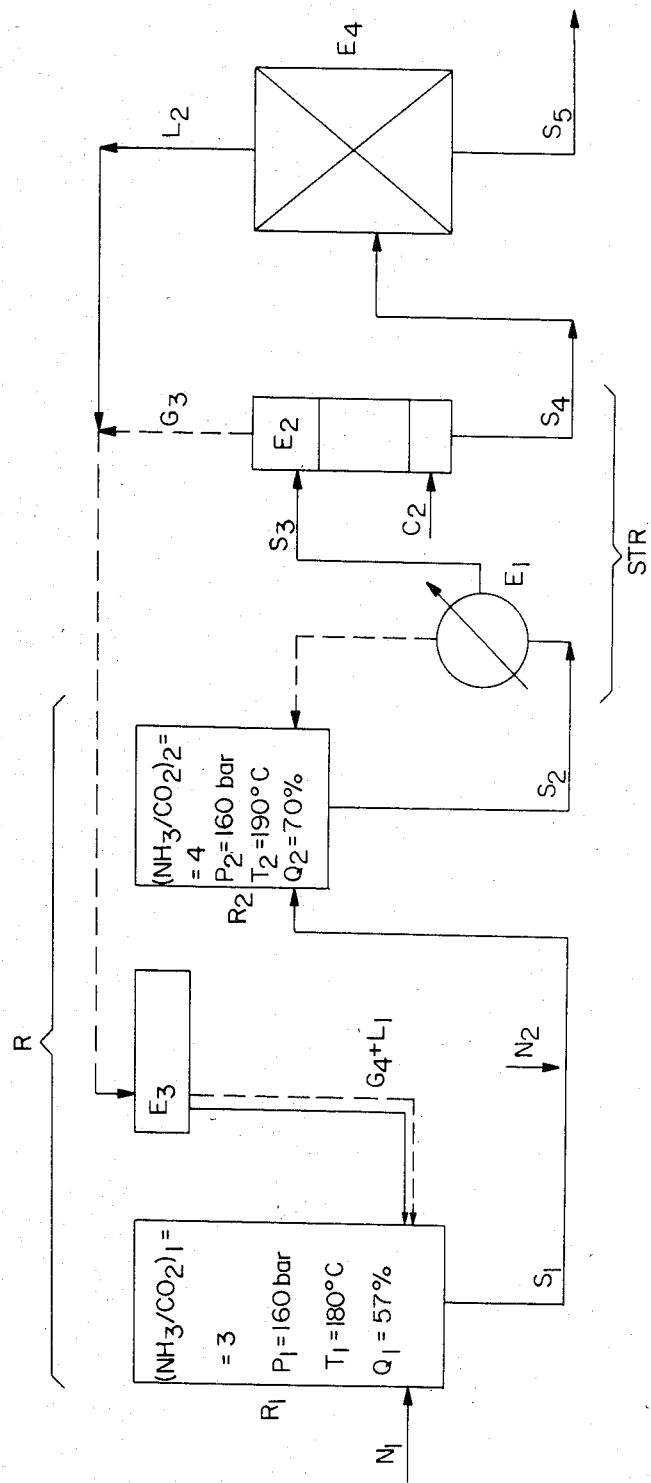

2. Isobaric operation (FIG. 3 and Table 2)

To the first reaction zone $R_1$, operating at $P_1=160$ bar and $T_1=180°$ C., are fed 25.82 moles of $NH_3$ (stream $N_1$) at 40° C. and the liquid-vapour mixture $G_4+L_1$ containing 21 moles of $CO_2$, 37.18 moles of $NH_3$ and 6 moles of $H_2O$ at 175° C.; the molar ratio $(NH_3/CO_2)_1$ is 3 and the conversion yeild $Q_1$ of $CO_2$ into urea is 57%. The ureau solution $S_1$ which feeds the second reaction zone $R_2$, therefore, consists of 12 moles of urea, 9 moles of $CO_2$, 39 moles of $NH_3$ and 18 moles of $H_2O$.

To the second reaction zone $R_2$, operating at $P_2=P_1=160$ bar and $T_2=190°$ C., are fed, besides solution $S_1$ from the first reaction zone $R_1$, vapours $G_1$ at 194° C. containing 2.8 moles of $CO_2$, 24.7 moles of $NH_3$ and 1 mole of $H_2O$ coming from the first treatment step $E_1$ also operating at $P_3=P_2=P_1=160$ bar and at $T_3=194°$ C.: To the second reaction zone $R_2$ are also fed 7.5 moles of $NH_3$ (stream $N_2$) at 40° C. and the molar ratio $(NH_3/CO_2)_2$ is 4; the $CO_2$ conversion yield $Q_2$ is 70%.

The urea solution $S_2$ containing 16.66 moles of urea, 7.14 moles of $CO_2$, 61.88 moles of $NH_3$ and 23.66 moles of $H_2O$ feeds the first treatment step $E_1$ where at $P_3=P_2=160$ bar and at $T_3=194°$ C. stream $G_1$ is separated, such stream containing 2.8 moles of $CO_2$, 24.7 moles of $NH_3$ and pb 1 mole of $H_2O$ fed directly to the second reaction zone $R_2$. Solution $S_3$, containing 16.66 moles of urea. 4.34 moles of $CO_2$. 37.19 moles of $NH_3$ and 22.66 moles of $H_2O$, feeds the second treatment step $E_2$ operating at $P_4=P_3=P_1=160$ bar and at $T_4=185°$ C., where by using stream $C_2$ containing 16.66 moles of $CO_2$ countercurrently, 2.84 moles of $CO_2$, 33.98 moles of $NH_3$ and 2 moles of $H_2O$ are separated from the urea solution. Gas $G_3$ discharged from $E_2$ consisting of 19.50 moles of $CO_2$, 33.98 moles of $NH_3$ and 2 moles of $H_2O$ at $P_4=P_3=P_1=160$ bar and at $T_5=190°$ C. feeds the condenser $E_3$ (carbamate condenser), also fed by solution $L_2$ (consisting of 1.5 moles of $CO_2$, 3.2 moles of $NH_3$ and 4 moles of $H_2O$), discharged from the final treatment system $S_5$ where the last traces of $CO_2$ and $H_2O$, still remaining in the solution from $E_2$, are finally separated. The mixed phase (vapours+carbamate solution) $G_4+L_1$ at 160 bar and 175° C. which formed in $E_3$ is recycled to the first reaction zone $R_1$. It contains 21 moles of $CO_2$, 37.18 moles of $NH_3$, 6 moles of $H_2O$. All the streams circulate in the isobaric system by gravity.

Figure 4:
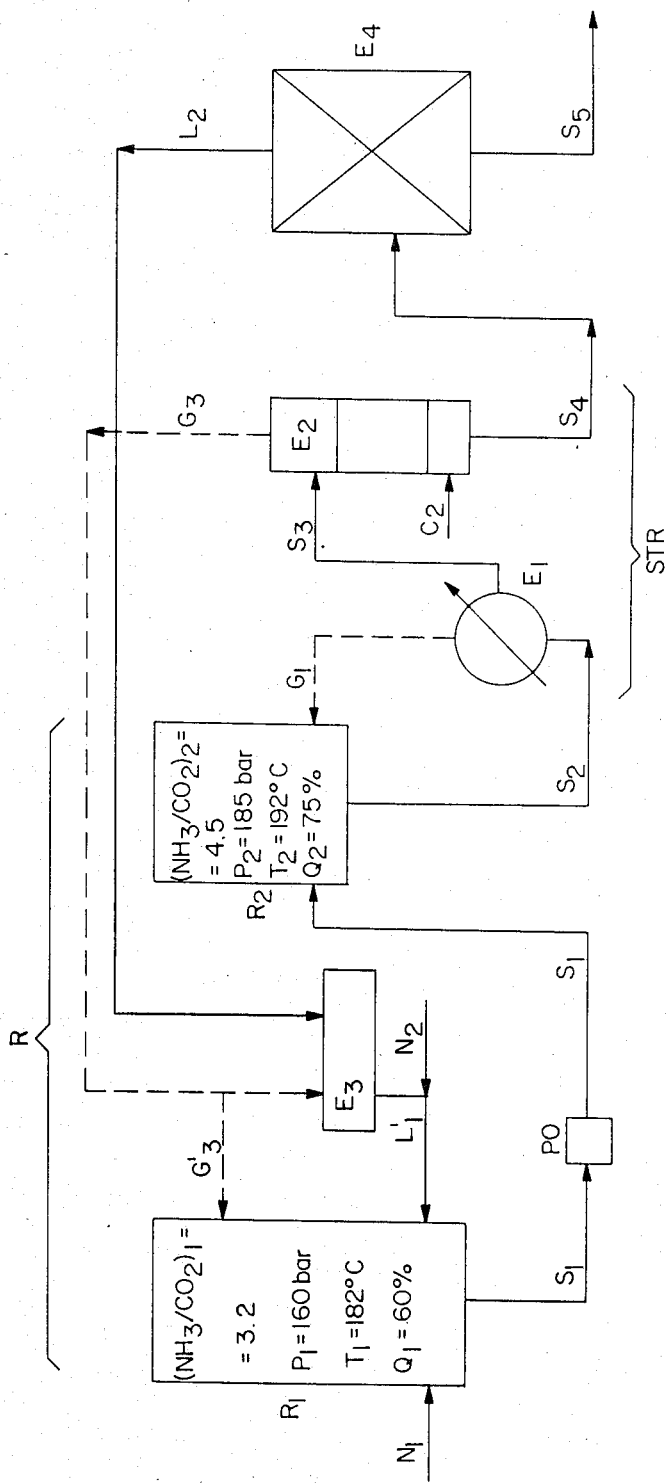

3. Non-isobaric operation (total condensation in the carbamate condenser) (FIG. 4 and Table 3)

As example 1, but with total condensation of part of the recycle vapours sent to the first reaction zone $R_1$, while the balance of the recycle vapours is directly recycled to the reactor.

In this case only a solution is recycled from condenser $E_3$ to the reactor, without vapour phase $L'_1$ ($G_4=O$) and the condenser is fed with only part of gas $G_3$, part of the same $G'_3$ being sent directly to the reactor.

TABLE 1

| LINES | $N_1$ | $S_1$ | $G_4+L_1$ | $S_1$ | $S_2$ | $G_1$ | $S_3$ | $S_4$ | $C_3$ | $S_5$ | $L_2$ | $C_2$ |
|---|---|---|---|---|---|---|---|---|---|---|---|---|
| STATE | LIQ | LIQ | LIQ + VAP | LIQ | LIQ | VAP | LIQ | LIQ | VAP | LIQ | LIQ | VAP |
| P - bar | 160 | 160 | 160 | 185 | 185 | 185 | 185 | 160 | 160 | — | 160 | 160 |
| T - °C. | 40 | 182 | 174 | 182 | 192 | 196 | 196 | 185 | 190 | — | — | 130 |

TABLE 1-continued

| LINES | $N_1$ | $S_1$ | $G_4 + L_1$ | $S_1$ | $S_2$ | $G_1$ | $S_3$ | $S_4$ | $C_3$ | $S_5$ | $L_2$ | $C_2$ |
|---|---|---|---|---|---|---|---|---|---|---|---|---|
| UREA | — | 12 | — | 12 | 16,66 | — | 16,66 | 16,66 | — | 16,66 | — | — |
| $CO_2$ | — | 8 | 20 | 8 | 5,54 | 2,2 | 3,34 | 1,5 | 18,5 | — | 1,5 | 16,66 |
| $NH_3$ | 33,32 | 40 | 30,68 | 40 | 66,68 | 36,0 | 30,68 | 3,2 | 27,48 | — | 3,2 | — |
| $H_2O$ | — | 18 | 6 | 18 | 23,66 | 1 | 22,66 | 20,66 | 2,0 | 16,66 | 4,0 | — |

TABLE 2

| LINES | $N_1$ | $S_1$ | $G_4 + L_1$ | $N_2$ | $S_2$ | $G_1$ | $S_3$ | $S_4$ | $C_3$ | $S_5$ | $L_2$ | $C_2$ |
|---|---|---|---|---|---|---|---|---|---|---|---|---|
| STATE | LIQ | LIQ | LIQ+VAP | LIQ | LIQ | VAP | LIQ | LIQ | VAP | LIQ | LIQ | VAP |
| P - bar | 160 | 160 | 160 | 160 | 160 | 160 | 160 | 160 | 160 | — | 160 | 160 |
| T - °C. | 40 | 180 | 175 | 40 | 190 | 194 | 194 | 185 | 190 | — | — | 130 |
| UREA | — | 12 | — | — | 16,66 | — | 16,66 | 16,66 | — | 16,66 | — | — |
| $CO_2$ | — | 9 | 21 | — | 7,14 | 2,8 | 4,34 | 1,5 | 19,50 | — | 1,5 | 16,66 |
| $NH_3$ | 25,82 | 39 | 37,18 | 7,5 | 61,88 | 24,7 | 37,18 | 3,2 | 33,98 | — | 3,2 | — |
| $H_2O$ | — | 18 | 6 | — | 23,66 | 1 | 22,66 | 20,66 | 2 | 16,66 | 4 | — |

TABLE 3

| LINES | $M_1$ | $S_1$ | $G_3$ | $S_1$ | $S_2$ | $G_1$ | $S_3$ | $S_4$ | $S_5$ | $L_2$ | $C_2$ |
|---|---|---|---|---|---|---|---|---|---|---|---|
| STATE | LIQ | LIQ | VAP | LIQ | LIQ | VAP | LIQ | LIQ | LIQ | LIQ | VAP |
| P - bar | 160 | 160 | 160 | 185 | 185 | 185 | 185 | 160 | 160 | 160 | 160 |
| T - °C. | 40 | 182 | 190 | 182 | 192 | 196 | 196 | 185 | — | — | 130 |
| UREA | — | 12 | — | 12 | 16,66 | — | 16,66 | 16,66 | 16,66 | — | — |
| $CO_2$ | — | 8 | 18,5 | 8 | 5,54 | 2,2 | 3,34 | 1,5 | — | 1,5 | 16,66 |
| $NH_3$ | 33,32 | 40 | 27,48 | 40 | 66,68 | 36 | 30,68 | 3,2 | — | 3,2 | — |
| $H_2O$ | — | 18 | 2 | 18 | 23,66 | 1 | 22,66 | 20,66 | 16,66 | 4 | — |

I claim:

1. In a process for the synthesis of urea of the type wherein ammonia and carbon dioxide are reacted in first and second reaction zones in series having each a different $NH_3/CO_2$ ratio under high temperature and high pressure with a large excess of ammonia to yield a reaction product including urea, water, carbamate, and unreacted ammonia and carbon dioxide, which is treated to decompose and separate carbamate and unreacted compounds from urea product, the improvement comprising a non-isobaric process of:
   (a) treating the reaction product from said in series second zone in first and second treatment steps to quantitatively decompose and separate carbamate and unreacted compounds in each treatment step and to form first and second treatment products, respectively;
   (b) at least partially condensing the second treatment product and recycling at least a part of the first treatment product separated in the first treatment step to the second reaction zone so that the vapors associated or added to the condensed product are sufficient to maintain an optimal temperature in said first zone;
   (c) recycling a composition and amount of the second treatment product separated in the second treatment step to the first reaction zone; said first and second treatment products being controlled so that optimal $NH_3/CO_2$ ratios and temperatures are maintained in the reaction zones by the recycled product.

2. The process of claim 1, wherein the first reaction zone and second treatment step are maintained at equal first pressures, the second reaction zone and the first treatment step are maintained at equal second pressures, and said second pressure is higher than said first pressure.

* * * * *